United States Patent
Mukumoto et al.

(10) Patent No.: US 9,232,792 B2
(45) Date of Patent: Jan. 12, 2016

(54) METHOD FOR PROMOTING PLANT GROWTH

(75) Inventors: Fujio Mukumoto, Takarazuka (JP);
Hiroaki Tamaki, Takarazuka (JP);
Mitsuhiko Iwakoshi, Takarazuka (JP);
Shintaro Kusaka, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 12 days.

(21) Appl. No.: 14/009,497

(22) PCT Filed: May 9, 2012

(86) PCT No.: PCT/JP2012/062440
§ 371 (c)(1),
(2), (4) Date: Oct. 2, 2013

(87) PCT Pub. No.: WO2012/153861
PCT Pub. Date: Nov. 15, 2012

(65) Prior Publication Data
US 2014/0031233 A1    Jan. 30, 2014

(30) Foreign Application Priority Data

May 10, 2011  (JP) .................................. 2011-104956

(51) Int. Cl.
*A01N 43/12* (2006.01)
*A01N 25/02* (2006.01)
*A01G 7/06* (2006.01)

(52) U.S. Cl.
CPC *A01N 43/12* (2013.01); *A01G 7/06* (2013.01); *A01N 25/02* (2013.01)

(58) Field of Classification Search
CPC .......... A01N 43/12; A01N 25/02; A01G 7/06
USPC ....................................................... 504/289
See application file for complete search history.

(56) References Cited

U.S. PATENT DOCUMENTS

| | | | |
|---|---|---|---|
| 4,391,627 A * | 7/1983 | Levitt .............................. | 504/213 |
| 5,110,829 A | 5/1992 | Kober et al. | |
| 5,118,680 A | 6/1992 | Müller et al. | |
| 5,298,482 A | 3/1994 | Tanaka et al. | |
| 5,304,657 A | 4/1994 | Toki et al. | |
| 5,965,749 A | 10/1999 | Brouwer | |
| 6,217,642 B1 | 4/2001 | Kunisch et al. | |
| 7,273,856 B2 | 9/2007 | Sisto et al. | |
| 7,732,477 B2 * | 6/2010 | Hendrix et al. ............... | 514/412 |
| 2004/0058957 A1 | 3/2004 | Tomita et al. | |
| 2005/0119325 A1 | 6/2005 | Hendrix et al. | |
| 2010/0004466 A1 | 1/2010 | Yi et al. | |
| 2010/0179061 A1 | 7/2010 | Saito | |

FOREIGN PATENT DOCUMENTS

| | | |
|---|---|---|
| JP | 3-34976 A | 2/1991 |
| JP | 4-234383 A | 8/1992 |
| JP | 4-342507 A | 11/1992 |
| JP | 11-512447 A | 10/1999 |
| JP | 2002-506860 A | 3/2002 |
| JP | 2002-114776 A | 4/2002 |
| JP | 2008-525523 A | 7/2008 |
| JP | 2010-506866 A | 3/2010 |
| WO | WO 2008/046533 A2 | 4/2008 |
| WO | WO 2008/146873 A1 | 12/2008 |
| WO | WO 2012/153860 A1 | 11/2012 |

OTHER PUBLICATIONS

The International Preliminary Report on Patentabiliy and Written Opinion of the International Searching Authority (Forms PCT/IB/326, PCT/IB/373, PCT/ISA/237), dated Nov. 21, 2013 for International Application No. PCT/JP2012/062440.
Burström et al., "Root Growth Effects of Indan, Indene, and Thionaphthene Derivatives", Physiologia Plantarum, vol. 9, 1956, pp. 502-514.
Sasaki et al., "Biosynthesis, biotechnological production and applications of 5-aminolevulinic acid", Appl Microbiol Biotechnol, vol. 58, 2002, pp. 23-29.
The Communication and Extended European Search Report, dated Oct. 1, 2014, issued in the corresponding European Patent Application No. 12782146.0.
XP-002729660: Allen et al., "An improved synthesis of substituted benzo[b] thiophenes using microwave irradiation," Database CA [Online], Chemical Abstracts Service, retrieved from STN Database, accession No. 2004:1048854, 2004.
The Second Office Action (including an English translation), dated Mar. 20, 2015, issued in the corresponding Chinese Patent Application No. 201280022117.9.
Communication pursuant to Article 94(3) EPC issued in the corresponding European Patent Application No. 12782146.0 on Sep. 15, 2015.
Allen et al., "An improved synthesis of substituted benzo[b]thiophenes using microwave irradiation," Tetrahedron Letters, vol. 45, 2004, pp. 9645-9647.
Patent Examination Report No. 1 issued in the corresponding Australian Patent Application No. 2012254404 on Oct. 27, 2015.

\* cited by examiner

*Primary Examiner* — John Pak
*Assistant Examiner* — Andriae M Holt
(74) *Attorney, Agent, or Firm* — Birch, Stewart, Kolasch & Birch, LLP

(57) ABSTRACT

Disclosed is a method for promoting the growth of a plant, comprising treating the plant with an effective amount of a compound represented by the following formula (1): wherein any one of $R_1$, $R_2$, $R_3$ and $R_4$ represents a trifluoromethyl group, and the others represent a hydrogen atom, or an agriculturally acceptable salt thereof.

(1)

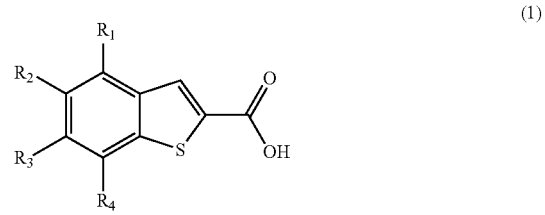

18 Claims, No Drawings

METHOD FOR PROMOTING PLANT GROWTH

TECHNICAL FIELD

The present application is filed claiming the priority of the Japanese Patent Application No. 2011-104956, the entire contents of which are herein incorporated by reference.

The present invention relates to a method for promoting the growth of plants.

BACKGROUND ART

Some chemical substances are known to show a promoting effect on the growth of plants, when the plants are treated with such a substance. For example, aminolevulinic acid shows a promoting effect on the growth of plants, when the compound is applied to the plants.

[Non-patent literature 1] "Biosynthesis, biotechnological production and applications of 5-aminolevulinic acid" K. Sasaki et al., (2002) Applied Microbial Biotechnology 58: pp. 23-29

DISCLOSURE OF INVENTION

An object of the present invention is to provide an excellent method for promoting the growth of plants, among others.

The present invention is based on the finding that treatment of a plant with a particular compound leads to promotion of the growth of the plant.

More specifically, the present invention provides:

[1] A method for promoting the growth of a plant, comprising treating the plant with an effective amount of a compound represented by the following formula (1):

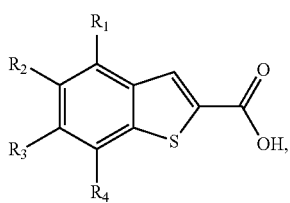

(1)

wherein any one of $R_1$, $R_2$, $R_3$ and $R_4$ represents a trifluoromethyl group, and the others represent a hydrogen atom, or an agriculturally acceptable salt thereof (hereinafter, the compound may be referred to as "the present compound", and the method may be referred to as "the method of the present invention");

[2] The method according to [1], wherein the compound represented by the formula (1) is a compound selected from the following compound group A:

<Compound Group A>
(1) 5-(trifluoromethyl)benzo[b]thiophene-2-carboxylic acid
(2) 6-(trifluoromethyl)benzo[b]thiophene-2-carboxylic acid
(3) 4-(trifluoromethyl)benzo[b]thiophene-2-carboxylic acid
(4) 7-(trifluoromethyl)benzo[b]thiophene-2-carboxylic acid

[3] The method according to [1] or [2], wherein the plant has been or is to be exposed to an abiotic stress;

[4] The method according to any one of [1] to [3], wherein the treatment of the plant is spraying treatment, soil treatment, seed treatment or hydroponic treatment;

[5] The method according to any one of [1] to [3], wherein the treatment of the plant is seed treatment;

[6] The method according to any one of [1] to [5], wherein the plant is rice, corn or wheat;

[7] The method according to any one of [1] to [6], wherein the plant is a transgenic plant;

[8] The method according to any one of [3] to [7], wherein the abiotic stress is high-temperature stress;

[9] The method according to any one of [3] to [7], wherein the abiotic stress is low-temperature stress;

[10] The method according to any one of [3] to [7], wherein the abiotic stress is drought stress;

[11] Use of the compound represented by the formula (1) or an agriculturally acceptable salt thereof, for promoting the growth of a plant.

and

[12] A composition for promoting the growth of a plant, comprising an effective amount of the compound represented by the formula (1) or an agriculturally acceptable salt thereof, and an inert component.

Effects of Invention

The method of the present invention allows for provision of an excellent method for promoting plant growth.

MODE FOR CARRYING OUT THE INVENTION

In the present invention, "growth promotion of a plant" (hereinafter may be referred to as "growth promotion") refers to an increase in the seedling establishment rate, number of healthy leaves, plant length, plant body weight, leaf area, number or weight of seeds or fruits, or number of set flowers or fruits, or the growth of roots.

Growth promotion may be quantified using the following parameters:

(1) Seedling Establishment Rate

Seeds of plants are sown, for example, in the soil, on a filter paper, on an agar culture medium or on sand, and then allowed to undergo cultivation for a given period of time. During the entire or partial cultivation period, abiotic stress is applied, and the percentage of surviving seedlings is examined.

(2) Number or Ratio of Healthy Leaves

With respect to each of plants, the number of healthy leaves is counted and the total number of healthy leaves is examined. Alternatively, the ratio of the number of healthy leaves to the number of all leaves of plants is examined.

(3) Plant Length

With respect to each of plants, the length from the base of the stem of the above-ground part to the branches and leaves at the tip is measured.

(4) Plant Body Weight

The above-ground part of each of plants is cut and the weight is measured to determine a fresh weight of plants. Alternatively, the cut sample is dried and the weight is measured to determine a dry weight of plants.

(5) Leaf Area

A photograph of plants is taken by a digital camera and the area of a green portion in the photograph is determined by image analysis software, for example, Win ROOF (manufactured by MITANI CORPORATION), or plants are visually evaluated to obtain a leaf area of plants.

(6) Leaf Color

After sampling leaves of plants, the chlorophyll content is measured using a chlorophyll gauge (for example, SPAD-502, manufactured by Konica Minolta Holdings, Inc.) to determine the leaf color. The plants are photographed with a digital camera and the green area in the photograph is measured by extracting color for quantification and using image analysis software, such as Win ROOF (manufactured by MITANI CORPORATION).

(7) Number or Weight of Seeds or Fruits

Plants are grown until they reach fructification or ripening of seeds or fruits, and then the number of fruits per plant is counted or the total weight of fruits per plant is measured. After cultivating plants until seeds undergo ripening, elements constituting the yield, such as the number of ears, ripening rate and thousand kernel weight are examined.

(8) Flower Setting Rate, Fruit Setting Rate, Seed Setting Rate and Seed Filling Rate After cultivating plants until they bear fruits, the number of flower setting and the number of fruit setting are counted to calculate the fruit setting rate % (100×number of fruit setting/number of flower setting). After seeds are ripe, the numbers of set seeds and filled seeds are counted to calculate the seed setting rate (%) ((Number of set seeds/Number of set flowers)×100) and the seed filling rate (%) ((Number of filled seeds/Number of set seeds)×100).

(9) Increase in the Growth of Roots

Plants are cultivated in soil or hydroponics. Then, the length of roots is measured or the roots are cut and measured the fresh weight of the roots.

In the method of the present invention, when a plant is treated with the present compound, the plant may be an entire plant or part thereof (e.g., stem and leaf, shoot, flower, fruit, panicle, seed, bulb, tuber and root). Also, the plant may be at any of the various stages of growth of the plant (e.g., the germination period, including preseeding time, seeding time, and the period before and after the seedling emergence after sowing; the vegetative growth period, including the nursery period, the time of seedling transplantation, the time of planting or nursing cuttings and the growth period after field planting; the reproductive growth period, including the periods before, during and after flowering, immediately before heading or the heading period; and the harvest period, including a period before the expected harvest date, a period before the expected ripening date and the time of initiation of fruit coloration). As used herein, the term bulb refers to a scaly bulb, corm, rhizome, root tuber and rhizophore. The seedlings may include cuttings and sugar cane stem cuttings.

The compound represented by the following formula (1):

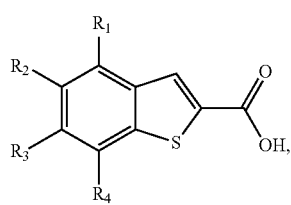

(1)

wherein any one of $R_1$, $R_2$, $R_3$ and $R_4$ represents a trifluoromethyl group, and the others represent a hydrogen atom, or an agriculturally acceptable salt thereof to be used in the method of the present invention may be produced by a known method or commercially available.

Specific examples of the compound represented by the formula (1) include the compounds (the present compounds 1 to 4) represented by the formula (1) wherein $R_1$, $R_2$, $R_3$ and $R_4$ are any one of the combinations of the substituents shown in Table 1.

TABLE 1

| The present compound | $R_1$ | $R_2$ | $R_3$ | $R_4$ |
|---|---|---|---|---|
| The present compound 1 | H | $CF_3$ | H | H |
| The present compound 2 | H | H | $CF_3$ | H |
| The present compound 3 | $CF_3$ | H | H | H |
| The present compound 4 | H | H | H | $CF_3$ |

The compound represented by the formula (1) may be a salt with an agriculturally acceptable base. Examples of the agriculturally acceptable salt of the compound represented by the formula (1) include the followings:

Metal salts such as alkali metal salts and alkaline-earth metal salts (e.g., salts with sodium, potassium, calcium, or magnesium); salts with ammonia; and salts with organic amines such as morpholine, piperidine, pyrrolidine, monoalkylamines, dialkylamines, trialkylamines, mono(hydroxyalkyl)amines, di(hydroxyalkyl)amines, and tri(hydroxyalkyl)amines.

When used in the method of the present invention, the present compound may be used alone or as a composition for promoting the growth of a plant formulated with various inert components (for example, formulation additives such as solid carriers, liquid carriers and surfactants), as described below.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; and synthetic inorganic materials such as synthetic hydrated silicon oxide; and as the liquid carrier, aromatic hydrocarbons such as xylene, alkylbenzene and methylnaphthalene; alcohols such as 2-propanol, ethylene glycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; nonionic surfactants such as polyoxyethylene alkyl aryl ethers, polyoxyethylene alkylpolyoxypropylene block copolymers and sorbitan fatty acid esters; and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

When plants are treated with the present compound in the method of the present invention, the treatment is performed by treating the plants or their cultivation areas with an effective amount of the present compound. In the treatment of plants or their cultivation areas, the present compound is applied in a single application or multiple applications.

The "effective amount" of the present compound as used herein means the amount of the present compound, which is capable of promoting the growth of a plant when treating the plant with the present compound.

Specifically, examples of the applications in the method of the present invention include treatment of foliage, floral organs or panicles, such as foliage spraying; treatment of soil (cultivation areas) before or after planting; treatment of seeds, such as seed sterilization, soaking or coating; treatment of seedlings; and treatment of bulbs such as seed potato.

Specifically, examples of the treatments of foliage, floral organs or panicles in the method of the present invention include treatment of the surface of plants, such as foliage spraying and trunk spraying. Also, examples of the treatments include spray treatment of floral organs or entire plants in the flowering stage including before, during and after flowering. For crop plants and the like, examples of the treatments include spray treatment of panicles or entire plants in the heading stage.

Examples of the soil treatment method in the method of the present invention include spraying onto the soil, soil incorporation, and perfusion of a chemical liquid into the soil (irrigation of chemical liquid, soil injection, and dripping of chemical liquid). Examples of the place to be treated include planting hole, furrow, around a planting hole, around a furrow, entire surface of cultivation lands, the parts between the soil and the plant, area between roots, area beneath the trunk, main furrow, growing soil, seedling raising box, seedling raising tray and seedbed. Examples of the treating period include before seeding, at the time of seeding, immediately after seeding, raising period, before settled planting, at the time of settled planting, and growing period after settled planting. In the soil treatment, a plurality of the present compounds may be simultaneously applied to a plant or a solid fertilizer, such as a paste fertilizer, containing the present compound may be applied to the soil. Also, the present compound may be mixed in an irrigation liquid, and, examples thereof include injecting to irrigation facilities (irrigation tube, irrigation pipe, sprinkler, etc.), mixing into the flooding liquid between furrows, mixing into a hydroponic medium and the like. Alternatively, an irrigation liquid may be mixed with the present compound in advance and, for example, used for treatment by an appropriate irrigating method including the irrigation method mentioned above and the other methods such as sprinkling and flooding.

The seed treatment in the method of the present invention refers to a process for treating seeds, bulbs and the like of plants of interest with the present compound; specific examples of the treatment include a spraying treatment by which a suspension of the present compound is atomized to be sprayed onto the surface of seeds or bulbs; a smear treatment by which the present compound in the form of a wettable powder, an emulsion, a flowable agent or the like is applied, directly or after being added with a small amount of water, onto seeds or bulbs; a soaking treatment in which seeds are soaked into a solution of the present compound for a certain period of time; a film coating treatment; and a pellet coating treatment.

Examples of the treatment of seedlings in the method of the present invention include spraying treatment of spraying to the entire seedlings a dilution having a proper concentration of active ingredients prepared by diluting the present compound with water, immersing treatment of immersing seedlings in the dilution, and coating treatment of adhering the present compound formulated into a dust formulation to the entire seedlings. Examples of the method of treating the soil before or after sowing seedlings include a method of spraying a dilution having a proper concentration of active ingredients prepared by diluting the present compound with water to seedlings or the soil around seedlings after sowing seedlings, and a method of spraying the present compound formulated into a solid formulation such as a granule to soil around seedlings after sowing seedlings.

The present compound may be mixed with a hydroponic medium in hydroponics, and may also be used as one of culture medium components in tissue culture. When the present compound is used for hydroponics, it can be dissolved or suspended in a conventionally used culture medium for hydroponics at a concentration within a range from 0.001 ppm to 1,000 ppm. When the present compound is used at the time of tissue culture or cell culture, it can be dissolved or suspended in a conventionally used culture medium for plant tissue culture, such as a Murashige and Skoog culture medium or a conventionally used culture medium for hydroponics, such as a Hoagland medium, at a concentration within a range from 0.001 ppm to 1,000 ppm. In this case, in accordance with a usual method, saccharides as a carbon source, various phytohormones and the like can be appropriately added.

When the present compound is used for treatment of plants or growing sites of plants, the treatment amount can vary according to the kind of plants to be treated, formulation form, treating period and meteorological conditions, but is usually within a rang from 0.1 g to 10,000 g, and preferably from 1 g to 1,000 g, in terms of an active ingredient amount, per 10,000 $m^2$. When the present compound is incorporated into the entire soil, the treatment amount is usually within a range from 0.1 g to 10,000 g, and preferably from 1 g to 1,000 g, in terms of an active ingredient amount, per 10,000 $m^2$.

At this time, an emulsion, a wettable powder, a flowable agent and a microcapsule are usually used for the treatment by spraying after dilution with water. In this case, the concentration of the active ingredient is usually within a range from 0.1 ppm to 10,000 ppm, and preferably from 1 ppm to 1,000 ppm. A dust formulation and a granule are usually used for the treatment as they are without dilution.

In the treatment of seeds, the treating amount of the present compound is generally 0.01 g to 1,000 g and preferably 0.1 g to 100 g per 100 kg of seeds.

The plants to which the method of the present invention can be applied include the following:

Crops: corn, rice, wheat, barley, rye, oat, sorghum, cotton, soybean, peanut, buckwheat, beet, oilseed rape, sunflower, sugar cane, tobacco, hop, etc.;

Vegetables: solanaceous vegetables (eggplant, tomato, potato, pepper, sweet pepper, etc.), cucurbitaceous vegetables (cucumber, pumpkin, zucchini, water melon, melon, oriental melon, etc.), cruciferous vegetables (Japanese radish, turnip, horseradish, kohlrabi, Chinese cabbage, cabbage, rape, leaf mustard, broccoli, cauliflower, etc.), asteraceous vegetables (burdock, crown daisy, artichoke, lettuce, etc.), liliaceous vegetables (green onion, onion, garlic, asparagus, etc.), apiaceous vegetables (carrot, parsley, celery, parsnip, etc.), chenopodiaceous vegetables (spinach, chard, etc.), Labiatae vegetables (Japanese basil, mint, basil, etc.), leguminous vegetables (pea, common bean, azuki bean, broad bean, chikbean, etc.), strawberry, sweet potato, Japanese yam, taro, *Amorphophallus konjac*, ginger, okra, etc.;

Fruits: pomaceous fruits (apple, pear, Japanese pear, Chinese quince, quince, etc.), stone fleshy fruits (peach, plum, nectarine, *Prunus mume*, cherry fruit, apricot, prune, etc.), *citrus* fruits (*Citrus unshiu*, orange, lemon, rime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, persimmon, olive, Japanese plum, banana, coffee, date palm, coconuts, oil palm, etc.;

Trees other than fruit trees: tea, mulberry, flowering trees (*Rhododendron indicum, camellia*, hydrangea, sasanqua, skimmia, cherry, tulip tree, crape myrtle, orange osmanthus, etc.), roadside trees (ash tree, birch, dogwood, eucalyptus, ginkgo biloba, lilac, maple, oak, poplar, redbud, liquidambar, sycamore, zelkova, Japanese arborvitae, fir, hemlock fir, juniper, pine, spruce, yew, elm, chestnut, etc.), *Viburnum awabuki, Podocarpus macrophyllus*, cedar, cypress, croton, Japanese spindle, Japanese photinia, etc.;

Grasses: *Zoysia* grasses (*Z. japonica, Z. pacifica*, etc.), bermudagrasses (Bermuda grass, etc.), bent grasses (redtop, creeping bent, colonial bent, etc.), bluegrasses (Kentucky bluegrass, rough bluegrass), fescues (tall fescue, Chewing's fescue, creeping red fescue), ryegrasses (darnel, rye grass, etc.), orchard grass, timothy grass, etc.; and Other plants: ornamental flowers (rose, carnation, chrysanthemum, eustoma, gypsophila, gerbera, marigold, salvia, petunia, verbena, tulip, aster, gentian, lily, pansy, cyclamen, orchid, lily of the valley, lavender, stock, ornamental cabbage, primula, poinsettia, gladiolus, cattleya, daisy, cymbidium, begonia, etc.), biofuel plants (Jatropha, safflower, *camellias*, switchgrass, miscanthus, reed canarygrass, giant cane, kenaf, cassava, willow, etc.), ornamental plants, etc.

Preferably, examples of the plants to which the method of the present invention can be applied include: tea, apple, pear, grape, cherry fruit, peach, nectarine, persimmon, Japanese plum, plum, soybean, lettuce, cabbage, tomato, eggplant, cucumber, water melon, common bean, pea, azuki bean, grass, oilseed rape, strawberry, almond, corn, sorghum, broad bean, Chinese cabbage, potato, peanut, rice, wheat, taro, *Amorphophallus konjac*, Japanese yam, Japanese radish, turnip, parsley, oriental melon, okra, ginger, lemon, orange, grapefruit, lime, blueberry, chestnut, hop, and basil. More preferably, examples of the plants include gramineous plants and solanaceous plants, particularly preferably gramineous plants, further more preferably rice, wheat and corn.

The aforementioned "plants" include genetically engineered plants obtained by introducing herbicide tolerance conferring genes, pest-selective toxin producing genes, disease resistance conferring genes, or abiotic stress reducing genes thereinto by genetic engineering techniques or hybridization breeding method, or stack varieties obtained by introducing a plurality of these genes thereinto.

The present compound may be applied simultaneously with a pesticide, a fungicide or a certain herbicide safener to a seed or a plant.

In the method of the present invention, the plant to be treated with the present compound may be a plant which has been or is to be exposed to an abiotic stress. Such "abiotic stress" may be quantified as "intensity of stress" according to the equation shown below. The intensity value may be 105 to 200, preferably 110 to 180, and more preferably 120 to 160.

"Intensity of stress"=100×"any one of the plant phenotypes in plants not being exposed to an abiotic stress"/"the one of the plant phenotypes in plants being exposed to the abiotic stress conditions"    Equation (I):

As used herein, an "abiotic stress" is defined as a stress that leads to growth inhibition of a plant, when the plant is exposed to an abiotic stress condition, such as temperature stress, i.e., high- or low-temperature stress, water stress, i.e., drought stress or excessive moisture stress, or salt stress, due to reduced physiological function of the cells of the plant and deterioration of the physiological state of the plant. The high-temperature stress refers to a stress that plants experience when they are exposed to a temperature exceeding the suitable temperature for their growth or germination. Specifically, the high-temperature stress may be caused under conditions in which the average growth temperature is 25° C. or higher, more harshly 30° C. or higher, and even more harshly 35° C. or higher in the environment in which the plants are cultivated. The low-temperature stress refers to a stress that plants experience when they are exposed to a temperature lower than the suitable temperature for their growth or germination. Specifically, the low-temperature stress may be caused under conditions in which the average growth temperature is 15° C. or lower, more harshly 10° C. or lower, and even more harshly 5° C. or lower in the environment in which the plants are cultivated. The drought stress refers to a stress that plants experience when they are exposed to a moisture environment that retards their growth by preventing water absorption due to a reduction in the water content of the soil caused by a shortage of rainfall or irrigation. Specifically, the drought stress may be caused under conditions in which the water content in the soil in which the plants are grown is 15% by weight or less, more harshly 10% by weight or less, and even more harshly 7.5% by weight or less, although these values may vary depending on the type of the soil, or in which the pF value of the soil in which the plants are grown is 2.3 or more, more harshly 2.7 or more, and even more harshly 3.0 or more, although these values may vary depending on the type of the soil. The excessive moisture stress refers to a stress that plants experience when they are exposed to a moisture environment in which the water content in the soil is excessively high, so that the growth of the plants is inhibited. Specifically, the excessive moisture stress may be caused under conditions in which the water content in the soil in which the plants are grown is 30% by weight or more, more harshly 40% by weight or more, and even more harshly 50% by weight or more, although these values may vary depending on the type of the soil, or in which the pF value of the soil in which the plants are grown is 1.7 or less, more harshly 1.0 or less, and even more harshly 0.3 or less, although these values may vary depending on the type of the soil. The pF value of soil may be determined according to the "Method for pF Value Measurement" on pages 61 and 62 of "Dojyo, Shokubutsu Eiyo, Kankyo Jiten (Encyclopedia of Soil, Plant Nutrition and Environment)" (TAIYOSHA Co., Ltd., 1994, Matsuzaka et al.). The salt stress refers to a stress that plants experience when they are exposed to an environment that retards their growth by preventing water absorption due to an increase in the osmotic pressure caused by accumulation of salts contained in the soil or hydroponic solution in which the plants are cultivated. Specifically, the salt stress may be caused under conditions in which the osmotic pressure potential due to the salts contained in the soil or hydroponic solution is 0.2 MPa (NaCl concentration of 2,400 ppm) or higher, harshly 0.25 MPa or higher, and more harshly 0.30 MPa or higher. The osmotic pressure in soil can be calculated according to Raoult's equation, shown below, by diluting the soil with water and analyzing the supernatant for salt concentration:

$\pi(atm) = cRT$    Raoult's Equation

R=0.082 (L·atm/mol·K)
T=Absolute temperature (K)
c=Ion molar concentration (mol/L)
1 atm=0.1 MPa

EXAMPLES

While the present invention will be more specifically described by way of formulation examples, seed treatment examples, and test examples in the following, the present invention is not limited to the following examples. In the following examples, the "part" represents "part by weight" unless otherwise specified.

Production Example 1

A mixture of 5.0 g of 2-fluoro-5-(trifluoromethyl)benzaldehyde, 3.3 g of methyl thioglycolate, 4.0 g of potassium carbonate and 50 ml of DMF was stirred at 60° C. for 2 hours, and then the reaction mixture was cooled to room temperature. To the reaction mixture was added water, and extracted with tert-butyl methyl ether 3 times. The combined organic layer was washed with water, followed by saturated aqueous sodium chloride solution. The mixture was dried over magnesium sulfate, and then concentrated under reduced pressure. The residue was recrystallized from methanol to obtain 6.3 g of methyl 5-(trifluoromethyl)benzo[b]thiophene-2-carboxylate.

A mixture of 300 mg of methyl 5-(trifluoromethyl)benzo[b]thiophene-2-carboxylate, 66 mg of lithium hydroxide monohydrate, 2 ml of water and 6 ml of methanol was stirred at 75° C. for 1 hour. The reaction mixture was cooled to room temperature, and then concentrated under reduced pressure. To the residue was added water, and then washed with tert-butyl methyl ether 3 times. To the aqueous layer was added concentrated hydrochloric acid, and then extracted with tert-butyl methyl ether 3 times. The combined organic layer was washed with saturated aqueous sodium chloride solution, dried over magnesium sulfate, and then concentrated under reduced pressure to obtain 280 mg of 5-(trifluoromethyl)benzo[b]thiophene-2-carboxylic acid (the present compound 1).

[The Present Compound 1]

$^1$H-NMR(CDCl$_3$) δ: 8.24 (s, 1H), 8.21 (s, 1H), 8.02 (d, J=8.7 Hz, 1H), 7.72 (d, J=8.7 Hz, 1H)

Production Example 2

A mixture of 1.11 g of 2-fluoro-4-(trifluoromethyl)benzaldehyde, 739 mg of methyl thioglycolate, 1.3 g of potassium carbonate and 20 ml of DMF was stirred at 140° C. for hours, and then the reaction mixture was cooled to room temperature. To the reaction mixture was added water, and then extracted with tert-butyl methyl ether 3 times. The combined organic layer was washed with water, followed by saturated aqueous sodium chloride solution. The mixture was dried over magnesium sulfate, and then concentrated under reduced pressure to obtain 848 mg of methyl 6-(trifluoromethyl)benzo[b]thiophene-2-carboxylate.

A mixture of 400 mg of methyl 6-(trifluoromethyl)benzo[b]thiophene-2-carboxylate, 105 mg of lithium hydroxide monohydrate, 3 ml of water and 9 ml of methanol was stirred at 75° C. for 2 hours. The reaction mixture was cooled to room temperature, and then concentrated under reduced pressure. To the residue was added water, and then washed with tert-butyl methyl ether 3 times. To the aqueous layer was added concentrated hydrochloric acid, and then extracted with chloroform 3 times. The combined organic layer was washed with saturated aqueous sodium chloride solution, dried over magnesium sulfate, and then concentrated under reduced pressure to obtain 355 mg of 6-(trifluoromethyl)benzo[b]thiophene-2-carboxylic acid (the present compound 2).

[The Present Compound 2]

$^1$H-NMR(CDCl$_3$) δ: 8.21 (s, 1H), 8.20 (s, 1H), 8.05-8.01 (m, 1H), 7.69-7.64 (m, 1H)

Production Example 3

A mixture of 1.00 g of 2-fluoro-6-(trifluoromethyl)benzaldehyde, 633 mg of methyl thioglycolate, 1.21 g of potassium carbonate and 15 ml of DMF was stirred at 130° C. for 2 hours. The reaction mixture was cooled to room temperature. To the reaction mixture was added water, and then extracted with tert-butyl methyl ether 3 times. The combined organic layer was washed with water, followed by saturated aqueous sodium chloride solution. The mixture was dried over magnesium sulfate, and then concentrated under reduced pressure obtain 480 mg of methyl 4-(trifluoromethyl)benzo[b]thiophene-2-carboxylate.

A mixture of 290 mg of methyl 4-(trifluoromethyl)benzo[b]thiophene-2-carboxylate, 60 mg of lithium hydroxide monohydrate, 2 ml of water and 6 ml of methanol was stirred at 75° C. for 1 hour. The reaction mixture was cooled to room temperature, and then concentrated under reduced pressure. To the residue was added water, and then washed with tert-butyl methyl ether 3 times. To the aqueous layer was added concentrated hydrochloric acid, and then extracted with chloroform 3 times. The combined organic layer was washed with saturated aqueous sodium chloride solution, dried over magnesium sulfate, and then concentrated under reduced pressure to obtain 240 mg of 4-(trifluoromethyl)benzo[b]thiophene-2-carboxylic acid (the present compound 3).

[The Present Compound 3]

$^1$H-NMR (DMSO-d$_6$) δ: 13.92 (br s, 1H), 8.47-8.43 (m, 1H), 8.04 (s, 1H), 7.92-7.88 (m, 1H), 7.74-7.68 (m, 1H)

Production Example 4

A mixture of 1.10 g of 2-fluoro-3-(trifluoromethyl)benzaldehyde, 663 mg of methyl thioglycolate, 1.03 g of potassium carbonate and 15 ml of DMF was stirred at 60° C. for 2 hours. The reaction mixture was cooled to room temperature. To the reaction mixture was added water, and then extracted with tert-butyl methyl ether 3 times. The combined organic layer was washed with water, followed by saturated aqueous sodium chloride solution. The mixture was dried over magnesium sulfate, and then concentrated under reduced pressure to obtain 1.34 g of methyl 7-(trifluoromethyl)benzo[b]thiophene-2-carboxylate.

A mixture of 800 mg of methyl 7-(trifluoromethyl)benzo[b]thiophene-2-carboxylate, 154 mg of lithium hydroxide monohydrate, 4 ml of water and 12 ml of methanol was stirred at 75° C. for 2 hours. The reaction mixture was cooled to room temperature, and then concentrated under reduced pressure. To the residue was added water, and then washed with tert-butyl methyl ether 3 times. To the aqueous layer was added concentrated hydrochloric acid, and then extracted with tert-butyl methyl ether 3 times. The combined organic layer was washed with saturated aqueous sodium chloride solution, dried over magnesium sulfate, and then concentrated under reduced pressure to obtain 632 mg of 7-(trifluoromethyl)benzo[b]thiophene-2-carboxylic acid (the present compound 4).

[The Present Compound 4]

$^1$H-NMR (DMSO-d$_6$) δ: 13.84 (br s, 1H), 8.37-8.32 (m, 1H), 8.29 (s, 1H), 7.98-7.94 (m, 1H), 7.72-7.66 (m, 1H)

Production Example 5

A mixture of 5.00 g of methyl 5-(trifluoromethyl)benzo[b]thiophene-2-carboxylate, 4.00 g of sodium carbonate, 20 ml of water and 60 ml of methanol was stirred at 80° C. for 3 hours. The reaction mixture was cooled to room temperature, and then concentrated under reduced pressure. The residue was recrystallized from water to obtain 5.10 g of sodium 5-(trifluoromethyl)benzo[b]thiophene-2-carboxylate (hereinafter referred to as "the present compound 5").

[The Present Compound 5]
$^1$H-NMR (DMSO-$d_6$) δ: 8.22 (s, 1H), 8.08 (d, J=8.5 Hz, 1H), 7.64 (s, 1H), 7.57 (d, J=8.5 Hz, 1H)

Production Example 6

A mixture of 5.00 g of methyl 5-(trifluoromethyl)benzo[b]thiophene-2-carboxylate, 2.93 g of potassium carbonate, 20 ml of water and 60 ml of methanol was stirred at 80° C. for 3 hours. The reaction mixture was cooled to room temperature, and then concentrated under reduced pressure. The residue was recrystallized from water to obtain 3.74 g of potassium 5-(trifluoromethyl)benzo[b]thiophene-2-carboxylate (hereinafter referred to as "the present compound 6").

[The Present Compounds 6]
$^1$H-NMR (DMSO-$d_6$) δ: 8.20 (s, 1H), 8.07 (d, J=8.5 Hz, 1H), 7.61 (s, 1H), 7.56 (d, J=8.5 Hz, 1H)

Production Example 7

A mixture of 300 mg of 5-(trifluoromethyl)benzo[b]thiophene-2-carboxylic acid, 80 mg of isopropylamine and 10 ml of tetrahydrofuran was stirred at room temperature for 1 hour. The reaction mixture was concentrated under reduced pressure to obtain 372 mg of isopropylammonium 5-(trifluoromethyl)benzo[b]thiophene-2-carboxylate (hereinafter referred to as "the present compound 7").

[The Present Compounds 7]
$^1$H-NMR (DMSO-$d_6$) δ: 8.23 (s, 1H), 8.09 (d, J=8.5 Hz, 1H), 7.65 (s, 1H), 7.58 (d, J=8.5 Hz, 1H), 3.34-3.26 (m, 1H), 1.18 (d, J=6.6 Hz, 6H)

Production Example 8

A mixture of 300 mg of 5-(trifluoromethyl)benzo[b]thiophene-2-carboxylic acid, 238 mg of laurylamine and 10 ml of tert-butyl methyl ether was stirred at room temperature for 1 hour. The reaction mixture was concentrated under reduced pressure to obtain 538 mg of laurylammonium 5-(trifluoromethyl)benzo[b]thiophene-2-carboxylate (hereinafter referred to as "the present compounds 8").

[The Present Compounds 8]
$^1$H-NMR (DMSO-$d_6$) δ: 8.23 (s, 1H), 8.09 (d, J=8.5 Hz, 1H), 7.65 (s, 1H), 7.58 (d, J=8.5 Hz, 1H), 2.78 (t, J=7.6 Hz, 2H), 1.57-1.50 (m, 2H), 1.26-1.21 (m, 18H), 0.84 (t, J=6.7 Hz, 3H)

Formulation Example 1

In a mixture of 35 parts of xylene and 35 parts of N,N-dimethylformamide is dissolved 10 parts of any one of the present compounds 1 to 8. To the mixture is added 14 parts of polyoxyethylene styryl phenyl ether and 6 parts of calcium dodecylbenzenesulfonate, and vigorously stirred to obtain each 10% emulsion.

Formulation Example 2

To a mixture of 4 parts of sodium lauryl sulfate, 2 parts of calcium lignosulfonate, 20 parts of a fine powder of synthetic hydrous silicon oxide and 54 parts of diatomaceous earth is added 20 parts of any one of the present compounds 1 to 8, and vigorously stirred to obtain each 20% wettable powder.

Formulation Example 3

To 2 parts of any one of the present compounds 1 to 8 are added 1 part of a fine powder of synthetic hydrous silicon oxide, 2 parts of calcium lignosulfonate, 30 parts of bentonite and 65 parts of kaolin clay, and the mixture is vigorously stirred. After that, to these mixtures is added an appropriate amount of water, further stirred, granulated with a granulator, and dried with ventilation to obtain each 2% granule formulation.

Formulation Example 4

Into an appropriate amount of acetone is dissolved 1 part of any one of the present compounds 1 to 8, and thereto are added 5 parts of a fine powder of synthetic hydrous silicon oxide, 0.3 parts of PAP and 93.7 parts of Fubasami clay. The mixture is vigorously stirred, and acetone is removed by evaporation to obtain each 1% powder formulation.

Formulation Example 5

Firstly, 10 parts of any one of the present compounds 1 to 8; 35 parts of a white carbon containing 50 parts of ammonium polyoxyethylene alkyl ether sulfate; and 55 parts of water are mixed. Then, the mixture is finely ground by a wet grinding method to obtain each 10% flowable formulation.

Formulation Example 6

Firstly, 0.1 parts of any one of the present compounds 1 to 8 is dissolved into 5 parts of xylene and 5 parts of trichloroethane. Then, the mixture is mixed with 89.9 parts of a deodorized oil to obtain each 0.1% oil formulation.

Test Example 1

Evaluation Test for Promotion of Root Growth in Hydroponics of Rice

<Test Plants>
Rice (cultivar: Nipponbare)
<Cultivation and Compound Treatment>
DMSO solutions containing each of the present compounds 1 to 3 at 10,000 ppm were prepared. A 1/10,000 volume of each DMSO solution containing each of the present compounds 1 to 3 at 10,000 ppm was added to a Hoagland solution for hydroponics at ¼ concentration (Hoagland and Arnon, California Agricultural Experiment Station 1950 Circular 347 pp. 34) to obtain a solution for hydroponics containing each of the present compounds 1 to 3 at 1 ppm. These solutions were used in the treated-group.

In a non-treated group, a solution for hydroponics obtained by adding a Hoagland solution for hydroponics at ¼ concentration to a 1/10,000 volume of DMSO was used.

The rice seeds were immersed in an aqueous solution of 1% sodium hypochlorite for 10 minutes, followed by 70% ethanol solution to sterilize their surfaces. After that, the seeds were washed with distilled water. The sterilized seeds were immersed in each solution for hydroponics containing the test compound at the given concentration, and incubated at a temperature of 28° C. for 3 days under dark conditions to stimulate the germination of the seeds.

Then, 30 ml of each solution for hydroponics containing the test compound at the given concentration was dispensed into a plastic tube (20 mm in diameter×113 mm in height) covered with a cardboard on the lateral surface for blocking a light. A float made of a styrene board and a vinyl mesh was placed on the water surface of each solution for hydroponics, and the rice seeds obtained after the stimulation of germination were placed on the float. The seeds were cultivated for 3 days under the conditions of an illuminance of 4,000 lux at the top of the tube, a temperature of 26° C., a humidity of 50%, and a day length of 16 hours.

<Evaluation Method>

The root length of the rice seedlings obtained after the cultivation was measured by using WinRHIZO system (manufactured by REGENT INSTRUMENTS). The average value of the root length in the treated group was calculated from the measurement values of 4 or 5 individuals. As a result, the root length in the treated group, wherein the plants were treated with the present compound 1, 2 or 3 (at a concentration of 1 ppm in each case), was much longer than that in the non-treated group.

Test Example 2

Evaluation Test for Reduction of Low-Temperature Stress by Immersion Treatment of Rice <Test Plants>

Rice (cultivar: Nipponbare)

<Cultivation>

A necessary amount of rice seeds was immersed in an aqueous solution of 1,000 ppm of Benlate, and incubated at 30° C. overnight under dark conditions. The aqueous solution of Benlate was replaced with distilled water, and the seeds were further incubated at 30° C. overnight under dark conditions to stimulate the germination of the seeds. A filter paper was placed on the holes of a plug tray having 406 holes, and the rice seeds obtained after the stimulation of germination were sown on the filter paper. To the rice seeds was added a kimura B solution for hydroponics (see Plant Science 119: 39-47 (1996)) at ½ concentration, and cultivated for 5 days in an artificial weather control room under the following conditions:

temperature: daytime 28° C./night 23° C., humidity: 70%, illuminance: 8,500 lux, and day length: 12 hours.

<Compound Treatment>

A DMSO solution of 1,000 ppm of the present compound 1 was prepared, and diluted with a kimura B solution for hydroponics at ½ concentration. The solution for hydroponics containing the compound was dispensed into the wells of a 24-well plate at 2 ml per well. One of the grown rice seedlings was placed into each well, and cultivated for 2 days on a cultivation shelf with a light under the following conditions:

temperature: 25° C., illuminance: 5,000 lux, and day length: 12 hours.

In a non-treated group, rice seedlings cultivated in the same manner as above except for using a solution for hydroponics containing 0.1% DMSO were used.

<Low-Temperature Stress Treatment>

The 24-well plate having the rice seedlings was moved into a cool box (MPR-1411, manufactured by SANYO Electric Co., Ltd.). Then, the seedlings were cultivated by using a cold cathode tube light for 5 days under the following conditions:

temperature: 4° C., illuminance: 3,500 lux, and day length: 12 hours.

<Evaluation Method>

The rice seedlings obtained after the low-temperature stress treatment was moved to a cultivation shelf with a light, and further cultivated for 4 days under the following conditions:

temperature: 25° C., illuminance: 5,000 lux, and day length: 12 hours

Four (4) days after the cultivation, the overground part of each rice plant in the treated group was taken a photograph, and the area of a green portion in the obtained image data was measured with image analysis software Win ROOF (manufactured by MITANI CORPORATION) to determine the green area of the overground part of the plant. In the treated group, the experiment was performed in duplication and the average value of the green area per individual was calculated. As a result, the green area of plants in the treated group, wherein the plants were treated with the present compound 1 at a concentration of 1 ppm, was much larger than that in the non-treated group.

Test Example 3

Evaluation Test for Promotion of Root Growth in Hydroponics of Rice

<Test Plants>

Rice (cultivar: Nipponbare)

<Cultivation and Compound Treatment>

DMSO solutions containing each of the present compounds 4 to 8 at 10,000 ppm were prepared. A 1/10,000 volume of each DMSO solution containing each of the present compounds 4 to 8 at 10,000 ppm was added to a Hoagland solution for hydroponics at ¼ concentration (Hoagland and Arnon, California Agricultural Experiment Station 1950 Circular 347 pp. 34) to obtain a solution for hydroponics containing each of the present compounds 4 to 8 at 1 ppm. These solutions were used in the treated-group.

In a non-treated group, a solution for hydroponics obtained by adding a Hoagland solution for hydroponics at ¼ concentration to a 1/10,000 volume of DMSO was used.

The rice seeds were immersed in an aqueous solution of 1% sodium hypochlorite for 10 minutes, followed by 70% ethanol solution to sterilize their surfaces. After that, the seeds were washed with distilled water. The sterilized seeds were immersed in each solution for hydroponics containing the test compound at the given concentration, and incubated at a temperature of 28° C. for 3 days under dark conditions to stimulate the germination of the seeds.

Then, 30 ml of each solution for hydroponics containing the test compound at the given concentration was dispensed into a plastic tube (20 mm in diameter×113 mm in height) covered with a cardboard on the lateral surface for blocking a light. A float made of a styrene board and a vinyl mesh was placed on the water surface of each solution for hydroponics, and the rice seeds obtained after the stimulation of germination were placed on the float. The seeds were cultivated for 3 days under the conditions of an illuminance of 4,000 lux at the top of the tube, a temperature of 26° C., a humidity of 50%, and a day length of 16 hours.

<Evaluation Method>

The root length of the rice seedlings obtained after the cultivation was measured by using WinRHIZO system (manufactured by REGENT INSTRUMENTS). The average value of the root length in the treated group was calculated from the measurement values of 4 or 5 individuals. As a result, the root length in the treated group, wherein the plants were treated with the present compound 4, 5, 6, 7 or 8 (at a concentration of 1 ppm in each case), was much longer than that in the non-treated group.

Test Example 4

Evaluation Test for Reduction of Low-Temperature Stress in Hydroponics of Tobacco <Test Plants>

Tobacco (*Nicotiana benthamiana*)

<Cultivation and Compound Treatment>

DMSO solutions containing each of the present compounds 1 to 4 at a concentration of 10,000 ppm were prepared. A 1/1,000 volume of each DMSO solution was added to a Murashige-and-Skoog medium (a medium containing 2.3 g of a mixture of salts for Murashige-and-Skoog medium (manufactured by Wako. Pure Chemical Industries, Ltd.), 200 mg of myoinositol (manufactured by Sigma-Aldrich), 2 mg of nicotinic acid (manufactured by Wako Pure Chemical Industries, Ltd.), 2 mg of pyridoxine hydrochloride (manufactured by Wako Pure Chemical Industries, Ltd.), 20 mg of thiamine hydrochloride (manufactured by Wako Pure Chemical Industries, Ltd.), 20 g of sucrose (manufactured by Wako Pure Chemical Industries, Ltd.), 1 g of MES (manufactured by DOJINDO LABORATORIES) in 1 L of water, adjusted to pH 5.8) at ½ concentration to obtain a medium containing the test compound at a concentration of 10 ppm. These media were used in the treated-group.

In a non-treated group, a medium obtained by adding a 1/1,000 volume of DMSO to a Murashige-and-Skoog medium at ½ concentration was used.

The seeds of tobacco (*Nicotiana benthamiana*) were sown on 5 µL of the medium, and incubated at 22° C. overnight. Thereto was added 45 µL of a medium containing each present compound at a concentration of 10 ppm, and cultivated for 7 days under the conditions of an illuminance of 4,000 lux, a temperature of 22° C. and a day length of 16 hours, thereby treating the seedlings of tobacco (*Nicotiana benthamiana*) with the test compound.

In the non-treated group, 45 µL of a medium obtained by adding a 1/1,000 volume of DMSO to a Murashige-and-Skoog medium at ½ concentration was added, and treated in the same manner as above.

<Low-Temperature Stress Treatment>

The seedlings of tobacco (*Nicotiana benthamiana*) treated with the present compounds were cultivated for 7 days under the conditions of an illuminance of 2,000 lux, a temperature of 1.5±1.0° C., and a day length of 16 hours, thereby subjecting to low-temperature stress treatment.

<Evaluation Method>

The plants of tobacco (*Nicotiana benthamiana*) subjected to low-temperature stress treatment was cultivated for 3 days under the conditions of an illuminance of 4,000 lux, a temperature of 22° C., and a day length of 16 hours, and then the green leaf area of the plants was visually evaluated. Completely dead plant was scored as 0, the plant without low-temperature stress treatment was scored as 5, the green area was rated on a 6-point scale in ⅕ increments, and the score of not less than 1 was regarded as effective in reducing the stress. As a result of visual evaluation, the green leaf area of plants in the treated group, wherein the plants were treated with the present compound 1, 2, 3 or 4 was much larger than that in the non-treated group.

Test Example 5

Evaluation Test for Reduction of Low-Temperature Stress by Treatment of Corn Seeds <Test Plants>

Corn (cultivar: Kuromochi)

<Seed Treatment>

A blank slurry solution containing 10% (V/V) color coat red (Becker Underwood, Inc.), 10% (V/V) CF-Clear (Becker Underwood, Inc.) and 1.66% Maxim 4FS (Syngenta) was prepared. A slurry solution was prepared by dissolving the present compound 1 in the blank slurry solution such that 0.5 g, 5 g or 50 g of the compound is applied to each 100 kg of corn seeds. In a 50-ml centrifuge tube (manufactured by BD Japan), 0.35 ml of the slurry solution was placed for each 14.4 g of corn seeds and stirred until the solution was dried, thereby coating the seeds. In addition, seeds were coated with the blank slurry solution and used as seeds for a non-treated group.

<Cultivation>

One of the treated corn seeds was sown in culture soil (AISAI) in each pot (55 mm in diameter×58 mm in height) and cultivated for 10 days under the conditions of a temperature of 27° C., an illuminance of 5,000 lux, and a day length of 16 hours. The grown seedlings were used for the test.

<Low-Temperature Stress Treatment Method>

The pots at 10 days after the sowing were placed into an artificial weather control room (VHT-2-15P-NC2-S, manufactured by Nippon Medical & Chemical Instruments Co., Ltd) and cultivated for 4 days under the following conditions: —temperature: 2.5±1° C., day length: 16 hours, and illuminance: 5,000 lux.

<Evaluation Method>

After the low-temperature stress treatment, the plants were cultivated for 4 days under the conditions of a temperature of 27° C., an illuminance of 5,000 lux, and a day length of 16 hours. Then, the fresh weight of the overground part of the plants was measured. The experiment was performed in four replications for each treatment condition and the average weight per individual was calculated.

As a result, the fresh weight of the overground part of plants in the treated group of applying 0.5 g, 5 g or 50 g of the present compound 1 to each 100 kg of seeds was much heavier than that in the non-treated group.

Test Example 6

Evaluation Test for Reduction of High-Temperature Stress by Spraying Treatment of Wheat <Test Plants>

Wheat (cultivar: Apogee)

<Spraying Treatment>

Five wheat seeds were sown in the culture soil (AISAI) in each plastic pot and cultivated for 28 days in an artificial weather control room under the conditions of a temperature of 18° C. in daytime/15° C. in night, and an illuminance of 7,000 lux. Before the stress test, 3 individuals per pot were removed.

To 0.5 mg of the present compound 1 were added 120 mg of a mixture (weight ratio 1:1) of white carbon and ammonium polyoxyethylene alkyl ether sulfate and 300 µl of water. The mixture was finely ground by a wet grinding method to obtain a flowable formulation of the present compound 1. This flowable formulation was diluted with 50 ml or 500 ml of water. The mixture was diluted with RINO (manufactured by NIHON NOHYAKU CO., LTD) as a spreading agent to 5,000-fold dilution to obtain a spray solution containing 10 ppm or 1 ppm of the present compound 1. A sufficient amount of the spray solution was applied to the wheat seedlings by using an automatic spraying machine.

In addition, a flowable formulation without the present compound 1 was prepared and then sprayed. This is called as a non-treated group.

<High-Temperature Stress Treatment>

The tested plants at 28 days after the sowing were cultivated for 7 days in an artificial weather control room under the conditions of a temperature of 36° C. in daytime/32° C. in night, a humidity of 50% in daytime/60% in night, an illuminance of 7,000 lux, and a day length of 12 hours.

<Evaluation Method>

After the high-temperature stress treatment, the plants were cultivated for 4 days in an artificial weather control room under the conditions of a temperature of 18° C. in daytime/15° C. in night, and a illuminance of 7,000 lux. Then, 90 days after the high-temperature stress treatment, the number and the weight of seeds in ears of the tested plants in 7 or 8 pots were measured, and the average values of the number and the weight of seeds per one ear were calculated. As a result, the number and the weight of seeds in the wheat plants treated with the present compound 1 at a concentration of 1 ppm or 10 ppm were much larger those in the non-treated group, in which the wheat plants were not treated with the present compound 1.

Test Example 7

Evaluation Test for Reduction of Drought Stress by Treatment of Rice Seeds

<Test Plants>

Rice (cultivar: Nipponbare)

<Treatment of Seeds>

A blank slurry solution containing 5% (V/V) color coat red (Becker Underwood, Inc.), 5% (V/V) CF-Clear (Becker Underwood, Inc.) and 1% Maxim XL (Syngenta) was prepared. A slurry solution was prepared by dissolving the present compound 1 in the blank slurry solution such that 50 g or 100 g of the compound is applied to each 100 kg of rice seeds. In a 50-ml centrifuge tube (manufactured by AGC TECHNO GLASS CO., LTD.), 0.3 ml of the slurry solution was placed for each 10 g of rice seeds and stirred until the solution was dried, thereby coating the seeds. In addition, seeds were coated with the blank slurry solution and used as seeds for a non-treated group.

<Cultivation>

A filter paper was placed on the holes of a plug tray having 406 holes, and the rice seeds treated above were sown on the filter paper. To the rice seeds was added a kimura B solution for hydroponics (see Plant Science 119: 39-47 (1996)) at ½ concentration, and cultivated for 17 days in an artificial weather control room under the conditions of temperature of 28° C. in daytime/23° C. in night, a humidity of 60%, an illuminance of 8500 lux, and a day length of 12 hours.

<Drought Stress Treatment>

Five rice seedlings grown as above were placed into an empty 35-ml flat-bottom test tube (manufactured by Assist/Sarstedt), and allowed to stand for 2 days without closing the top cover under the conditions of a temperature of 28° C. in daytime/23° C. in night, a humidity of 60%, an illuminance of 8,500 lux, and a day length of 12 hours.

<Evaluation Method>

The plants obtained after the drought stress treatment were placed into a centrifuge tube (manufactured by AGC TECHNO GLASS CO., LTD.) containing 100 ml of a Hoagland solution for hydroponics (Hoagland and Arnon, see California Agricultural Experiment Station 1950 Circular 347 pp. 34), and cultivated for 14 days under the conditions of a temperature of 28° C. in daytime/23° C. in night, a humidity of 60%, an illuminance of 8,500 lux, and a day length of 12 hours.

Fourteen (14) days after the treatment, the fresh weight of the overground parts of five test plants in each treated group was measured. The experiment was performed in three replications in each treated group and the average value was calculated. As a result, the fresh weight of the overground part of plants in the treated group of using 50 g or 100 g of the present compound 1 per 100 kg of seeds was much heavier than that in the non-treated group.

INDUSTRIAL APPLICABILITY

Use of the method of the present invention allows for effective promotion of plant growth.

The invention claimed is:

1. A method for promoting the growth of a plant, comprising treating the plant with an effective amount of a compound represented by the following formula (1):

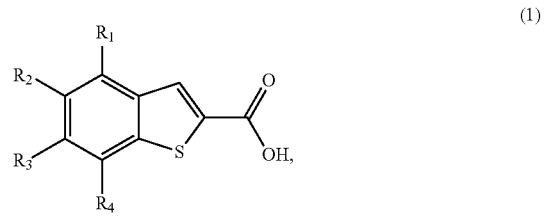

wherein any one of $R_1$, $R_2$, $R_3$ and $R_4$ represents a trifluoromethyl group, and the others represent a hydrogen atom, or an agriculturally acceptable salt thereof.

2. The method according to claim 1, wherein the compound represented by the formula (1) is a compound selected from the group consisting of
(1) 5-(trifluoromethyl)benzo[b]thiophene-2-carboxylic acid,
(2) 6-(trifluoromethyl)benzo[b]thiophene-2-carboxylic acid,
(3) 4-(trifluoromethyl)benzo[b]thiophene-2-carboxylic acid, and
(4) 7-(trifluoromethyl)benzo[b]thiophene-2-carboxylic acid.

3. The method according to claim 1, wherein the plant has been or is to be exposed to an abiotic stress.

4. The method according to claim 1, wherein the treatment of the plant is spraying treatment, soil treatment, seed treatment or hydroponic treatment.

5. The method according to claim 1, wherein the treatment of the plant is seed treatment.

6. The method according to claim 1, wherein the plant is rice, corn or wheat.

7. The method according to claim 1, wherein the plant is a transgenic plant.

8. The method according to claim 3, wherein the abiotic stress is high-temperature stress.

9. The method according to claim 3, wherein the abiotic stress is low-temperature stress.

10. The method according to claim 3, wherein the abiotic stress is drought stress.

11. The method according to claim 2, wherein the plant has been or is to be exposed to an abiotic stress.

12. The method according to claim 2, wherein the treatment of the plant is spraying treatment, soil treatment, seed treatment or hydroponic treatment.

13. The method according to claim 3, wherein the treatment of the plant is spraying treatment, soil treatment, seed treatment or hydroponic treatment.

14. The method according to claim 2, wherein the treatment of the plant is seed treatment.

15. The method according to claim 3, wherein the treatment of the plant is seed treatment.

16. The method according to claim 2, wherein the plant is rice, corn or wheat.

17. The method according to claim 3, wherein the plant is rice, corn or wheat.

18. The method according to claim 4, wherein the plant is rice, corn or wheat.

\* \* \* \* \*